United States Patent
Klingenbeck-Regn

(10) Patent No.: US 7,162,064 B2
(45) Date of Patent: *Jan. 9, 2007

(54) METHOD FOR OPERATING A COMPUTED TOMOGRAPHY DEVICE

(75) Inventor: Klaus Klingenbeck-Regn, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 648 days.

This patent is subject to a terminal disclaimer.

(21) Appl. No.: 10/258,303

(22) PCT Filed: Apr. 23, 2001

(86) PCT No.: PCT/DE01/01536

§ 371 (c)(1),
(2), (4) Date: Oct. 23, 2002

(87) PCT Pub. No.: WO01/80740

PCT Pub. Date: Nov. 1, 2001

(65) Prior Publication Data

US 2004/0013293 A1 Jan. 22, 2004

(30) Foreign Application Priority Data

Apr. 25, 2000 (DE) .............................. 100 20 258

(51) Int. Cl.
- G06K 9/00 (2006.01)
- A61B 6/00 (2006.01)
- G01N 23/00 (2006.01)
- G21K 1/12 (2006.01)
- H05G 1/60 (2006.01)
- G06K 9/36 (2006.01)

(52) U.S. Cl. ...................... 382/131; 382/130; 382/132; 382/154; 382/285; 378/4; 378/21; 378/162

(58) Field of Classification Search ........ 382/130–132, 382/128, 154, 285; 378/4, 8, 15, 16, 18, 378/20, 21, 95, 162

See application file for complete search history.

(56) References Cited

U.S. PATENT DOCUMENTS

| | | | |
|---|---|---|---|
| 5,218,623 A | 6/1993 | Toki et al. | |
| 5,345,513 A * | 9/1994 | Takeda et al. | ............... 382/132 |
| 5,825,908 A | 10/1998 | Pieper et al. | |
| 5,995,580 A | 11/1999 | Schaller | |
| 6,292,527 B1 | 9/2001 | Guendel | |
| 6,512,808 B1 * | 1/2003 | Klingenbeck-Regn | ....... 378/18 |

* cited by examiner

Primary Examiner—Bhavesh M. Mehta
Assistant Examiner—Manav Seth
(74) Attorney, Agent, or Firm—Schiff Hardin LLP

(57) ABSTRACT

A method for operating a computed tomograph device is provided by which volume data pertaining to a volume area of a test object can be recorded. A marking for identifying a reconstruction area to be reconstructed is faded into an x-ray shadow image containing the volume area, wherein a split image of the beginning and/or end of the reconstruction area is reconstructed from the volume data in order to verify the position of the reconstruction area.

6 Claims, 5 Drawing Sheets

METHOD FOR OPERATING A COMPUTED TOMOGRAPHY DEVICE

BACKGROUND OF THE INVENTION

1. Field of the Invention

The present invention relates to a method of operating a (CT) computed tomography device, by means of which volume data with respect to a volume region of a test object can be recorded.

2. Description of the Prior Art

Normally, before the definition of a region with respect to which volume data are to be recorded, for example by means of a spiral scan, an X-ray shadow image (topogram) is recorded, using which the scanning area of the following spiral scan is defined graphically. The definition of a scanning area is carried out by means of graphical marking of a region, inter alia a rectangular region, in the X-ray shadow image, which includes the interesting region of the test object. The length of the rectangle defines the length of the spiral scan, the width of the rectangle defines the width of the field of view represented in the CT image.

When defining a number of spiral scans, the above procedure is applied repeatedly.

German OS 199 25 395, which claims earlier priority but is not a prior publication, discloses a method of operating a CT device, in which volume data obtained in the course of a volume scan is used to extract the data needed for the reconstruction of an X-ray shadow image.

U.S. Pat. No. 5,995,580 describes a method of reconstructing volume data pertaining to a volume region that is limited in the direction of the system axis of a CT device, in which the start and end surfaces of the volume region are curved.

SUMMARY OF THE INVENTION

An object of the present invention is to provide a method of the type initially cited which makes it easier for an operator to obtain the diagnostic information desired in each case.

The above object is achieved in accordance with the principles of the present invention in a method for operating a CT device wherein volume data pertaining to a volume region of a test subject are obtained, having the following steps:

(a) recording volume data pertaining to a volume region of a test object and creating and displaying an X-ray shadow image of the volume region from the volume data;

(b) inserting at least one marking into the X-ray shadow image for identifying a reconstruction region with respect to which image data are to be reconstructed from the volume data;

(c) reconstructing and displaying a slice of at least one of a start and an end of the reconstruction region from the volume data; and (d) reconstructing image data pertaining to each reconstruction region.

It is therefore possible, within the volume data recorded during a spiral scan, for example, to mark one or more regions with respect to which a reconstruction of image data is then carried out. In this case, there is the possibility, beyond the monitoring of the position of the reconstruction regions provided on the basis of the X-ray shadow image, of performing monitoring on the basis of slices which illustrate the start and/or end of a reconstruction region, that is to say slices representing a layer of the test object containing a start or end, in order if required to be able to correct the position of the reconstruction regions.

The ordering of the items in method step a) need not necessarily be precisely as set forth above. Instead, the recording of the volume data can be carried out both before and after the creation and display of the X-ray shadow image.

In a preferred embodiment of the invention, at least one reconstruction region is assigned at least one reconstruction parameter, and the reconstruction of image data with respect to the reconstruction region is carried out by taking into account the reconstruction parameters assigned to it; according to one variant of the invention, the reconstruction parameters typical of the respective reconstruction region being the layer thickness on which the reconstruction is based—the so-called reconstructed layer thickness—and/or the convolution core to be used in the reconstruction. The assignment of further or different reconstruction parameters is possible within the scope of the invention.

The invention supports the clinical application of CT devices by means of easier operation and an optimized sequence, in particular in those applications for which it is necessary, for the diagnosis of an organ, for example, to reconstruct part sections of the organ with a different layer thickness than other part sections of the same organ, since this is carried out on the basis of volume data which has been obtained during a single spiral scan, since the marking of the reconstruction regions is carried out simultaneously in a single operation and in a single X-ray shadow image, and since, on the basis of the slices illustrating the start and/or end of a reconstruction region, additional monitoring of a plurality of correct position of the reconstruction regions is possible.

If a number of reconstruction regions are marked, these can at least partly overlap one another, according to a variant of the invention. This offers the advantage that regions of the test object that are contained in a plurality of reconstruction regions do not have to be scanned repeatedly and, in the process, be subjected to X radiation.

In a preferred embodiment of the invention, the volume data is recorded in the form of a spiral scan. However, there is also the possibility of obtaining the volume data in another way, for example by means of sequential scanning.

Modern multilayer CT devices, that is to say CT devices whose detector system has a plurality of rows of detector elements, are capable of scanning volumes with a high axial resolution, that is to say close collimation (low layer thickness of the layers of the test object scanned by means of the individual lines of the detector system) in a single spiral scan. This scanning results in volume data from which, for example, images of thin or thick layers can subsequently be reconstructed. It is therefore possible for the user to obtain various diagnostic information from volume data recorded during a single spiral scan with close collimation: thinner layers in order to be able to obtain information about high-contrast structures, for example bones, vessels filled with contrast media, bronchiae containing air or prepared intestine, and thicker layers, in order to be able to obtain information about low-contrast structures, for example soft tissue parts.

A typical example is a spiral scan of the skull with a collimation of 4*1 mm. For the base of the skull, the radiologist needs layer thicknesses of 3 mm or 4 mm thickness, for the cerebrum, layer thicknesses of 5 mm to 8 mm are normal. In the case of simultaneous CTA (CT angiography), the thinnest layers of 1 mm are required, for example for the display of the Circulus Willisis.

Similar requirements arise during the examination of other organs, such as lungs, with high-resolution images of 1 mm layer thickness and standard images of 5 mm layer thickness, or CTA of the abdomen or examination of the entire aorta with the various arterial exits.

If a number of spiral scans is carried out, such as in the case of a multiphase liver examination, then the procedure can be carried out in the manner described above with respect to each individual spiral scan.

DESCRIPTION OF THE PREFERRED EMBODIMENTS

Figure 1:
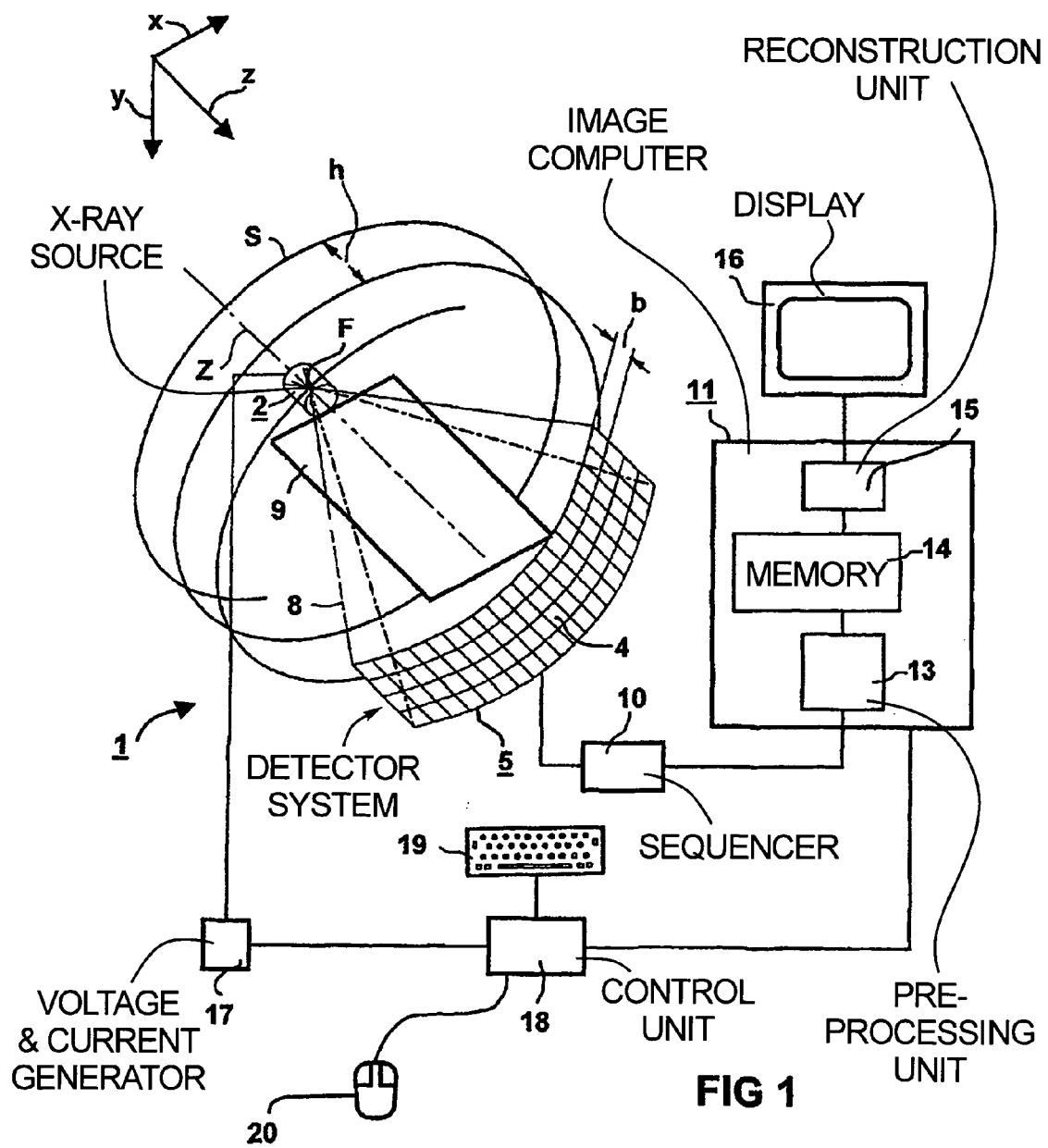
FIG. 1 illustrates a CT device for conducting the inventive method in a partly perspective, partly block-diagram illustration.
Figure 2:
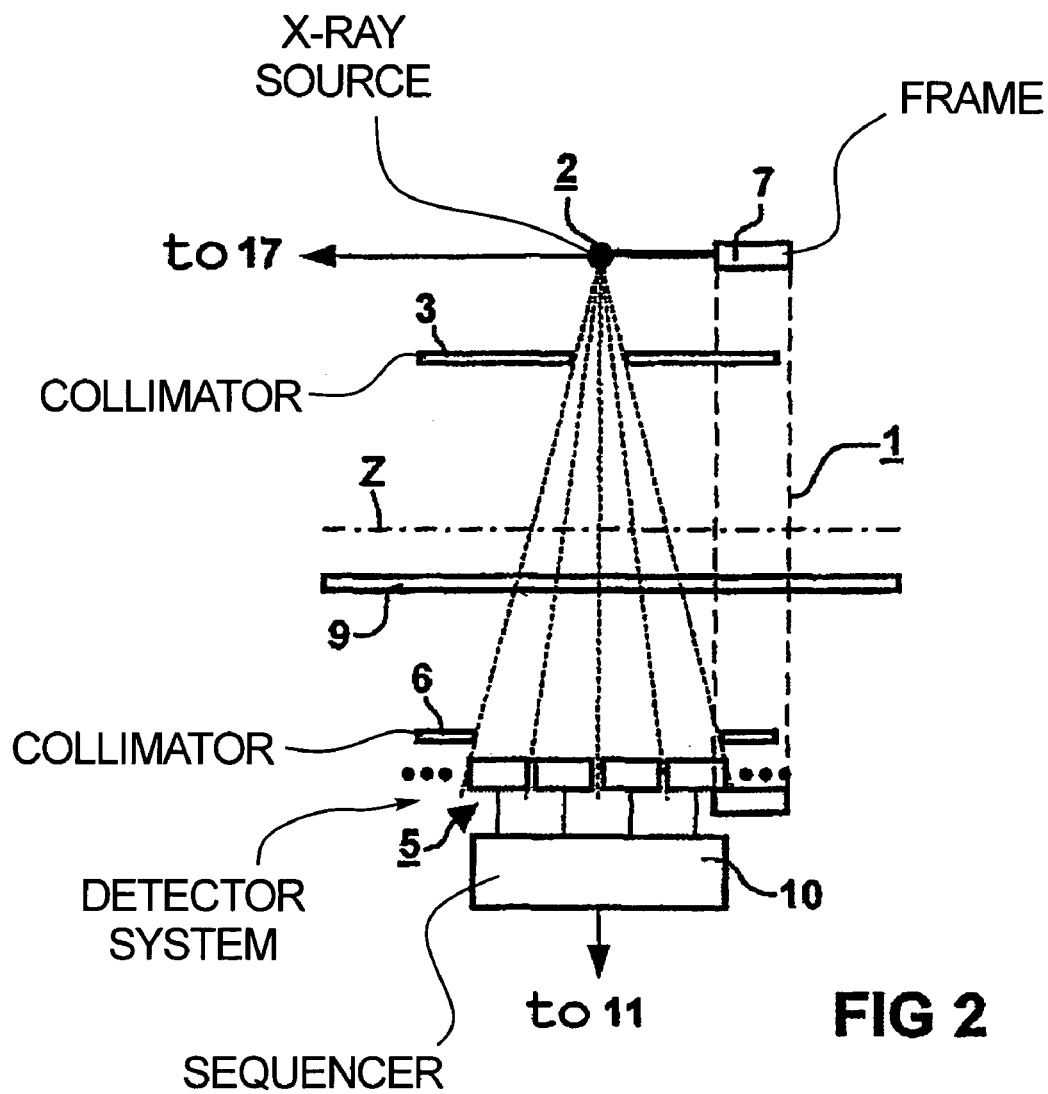
FIG. 2 is a longitudinal section through the device of FIG. 1.

In FIGS. 1 and 2, a multilayer CT device of the third generation suitable for carrying out the method according to the invention is illustrated. Its measuring arrangement, designated overall by 1, has an X-ray source, designated overall by 2, with a collimator 3 (FIG. 2) placed in front of it close to the source, and a detector system 5 constructed as a two-dimensional array of a number of rows and columns of detector elements—one of these is designated 4 in FIG. 1 having a collimator 6 (FIG. 2) arranged in front of the system, close to the detector. The X-ray source 2 with the collimator 3 on the one hand, and the detector system 5 with the collimator 6 on the other hand are fitted in a manner which can be seen from FIG. 2 opposite each other on a rotary frame 7 in such a way that a pyramidal X-ray beam originating from the X-ray source during the operation of the CT device 2, collimated by the adjustable collimator 3 and whose edge beams are designated by 8 strikes the detector system 5. In the process, the collimator 6 is set to correspond to the cross section of the X-ray beam set by means of the collimator 3, such that only that region of the detector system 5 is exposed which can be struck directly by the X-ray beam. In the operating state illustrated in FIGS. 1 and 2, these are four rows of detector elements. The fact that there are further rows of detector elements covered by the collimator 6 is indicated dotted in FIG. 2.

The rotary frame 7 can be set rotating about a system axis designated by Z by means of a drive device, not illustrated. The system axis Z runs parallel to the z-axis of a three-dimensional rectangular coordinate system illustrated in FIG. 1.

The columns of the detector system 5 likewise run in the direction of the z-axis, while the rows, whose width b is measured in the direction of the z-axis and is 1 mm, for example, run transversely with respect to the system axis Z and the z-axis.

In order to be able to bring a test object, for example a patient, into the beam path of the X-ray beam, a mounting device 9 is provided, which can be displaced parallel to the system axis Z, that is to say in the direction of the z-axis.

In order to record volume data of a test object located on the mounting device 9, for example a patient, the test object is scanned by a large number of projections from various projection directions being recorded while the measuring unit 1 is moved around the system axis Z. The data supplied by the detector system 5 therefore contains a large number of projections.

During the continuous rotation of the measuring unit 1 around the system axis Z, at the same time the mounting device 9 is displaced continuously relative to the measuring unit 1 in the direction of the system axis Z, there being synchronization between the rotational movement of the rotary frame 7 and the translational movement of the mounting device 9 with the effect that the ratio between translation and rotation speed is constant and this constant ratio is adjustable, by a value for the advance h of the mounting device 9 per revolution of the rotary frame 7 being selected which ensures complete scanning of the interesting volume of the test object. The focus F of the X-ray source 2 therefore moves, as viewed from the test object, on a helical spiral path, designated by S in FIG. 1, around the system axis Z, for which reason the type of recording of volume data described is also designated spiral scanning or a spiral scan. The volume data supplied in the process by the detector elements of each row of the detector system 5, which data is projections in each case associated with a specific row of the detector system 5 and a specific position with respect to the system axis Z, is read out in parallel, serialized in a sequencer 10 and transmitted to an image computer 11.

Following preprocessing of the volume data in a preprocessing unit 13 of the image computer 11, the resultant data stream passes to a memory 14, in which the volume data corresponding to the data stream are stored.

The image computer 11 contains a reconstruction unit 15 which reconstructs image data from the volume data, for example in the form of slices of desired layers of the test object, in accordance with methods known to those skilled in the art. The image data reconstructed by the reconstruction unit 15 is stored in a memory 14 and can be displayed on a display unit 16, for example a video monitor, connected to the image computer 11.

The X-ray source 2, for example an X-ray tube, is supplied with the necessary voltages and currents by a generator unit 17. In order to be able to set these to the respectively necessary values, the generator unit 17 is assigned a control unit 18 with keyboard 19 and mouse 20, which permits the necessary settings.

In addition, the other operation and control of the CT device is carried out by means of the control unit 18 and the keyboard 19 and also the mouse 20, which is illustrated by the fact that the control unit 18 is connected to the image computer 11.

In order to restrict the recording of volume data to the diagnostically necessary region, and therefore to save the test object from unnecessary X-radiation, before the volume data is recorded, an X-ray shadow image of the diagnostically relevant region of the test object is prepared. For this purpose, with the X-ray source activated but without rotation of the measuring unit 1 about the system axis Z, the mounting device 6 is displaced in the direction of the system axis 7 relative to the measuring unit 1 by that amount which is required to record the diagnostically relevant region of the test object. The output data from the detector system 5 which arise in the process are transmitted in serialized form to the image computer 11, which uses the data, in accordance with known algorithms, to calculate an X-ray shadow image (topogram), display it on the display unit 16 and if desired store it in the memory 14. The display of an X-ray shadow image designated RSB is illustrated in FIG. 3, which shows the monitor of the display unit 16.

Figure 3:
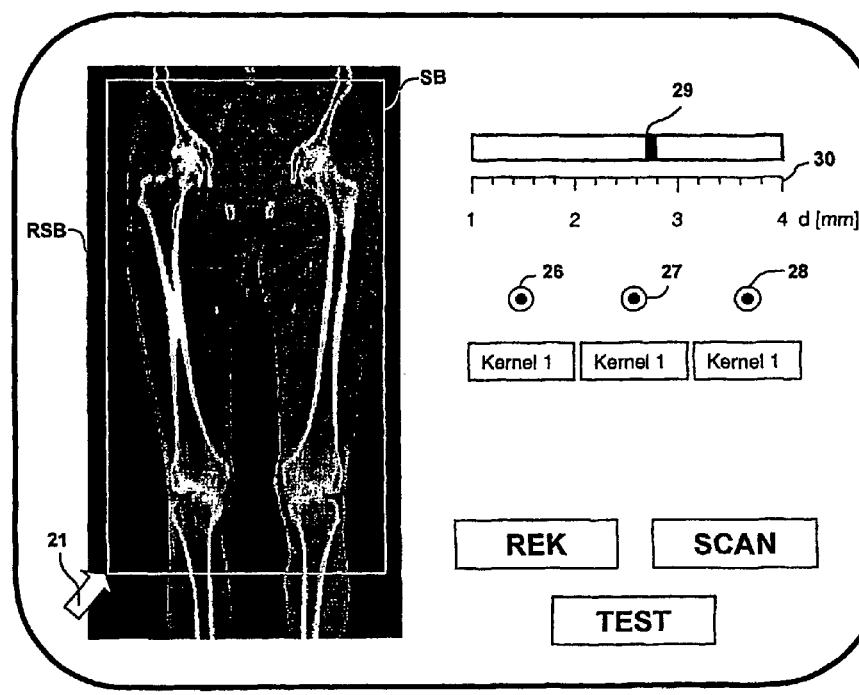
FIGS. 3 through 5 respectively show displays at the operator interface of the CT device of FIGS. 1 and 2, as occur during the execution of the inventive method.

As additionally can be seen from FIG. 3, it is possible, by means of the mouse 20, the associated cursor is designated 21, to mark a rectangular region SB in the X-ray shadow image RSB, with respect to which region volume data permitting the reconstruction of image data is to be recorded.

As soon as an operator activates a corresponding icon designated SCAN and illustrated on the monitor, by using the cursor 21 and actuating the left key of the mouse 20, the control unit uses the position and size of the marked region SB to calculate the start and end point of the displacement of the mounting device 9 in the direction of the system axis Z which is necessary to be able to record the volume data permitting the reconstruction of image data with respect to the marked region SB in the course of a spiral scan, and arranges for the appropriate spiral scan to be carried out.

Figure 4:
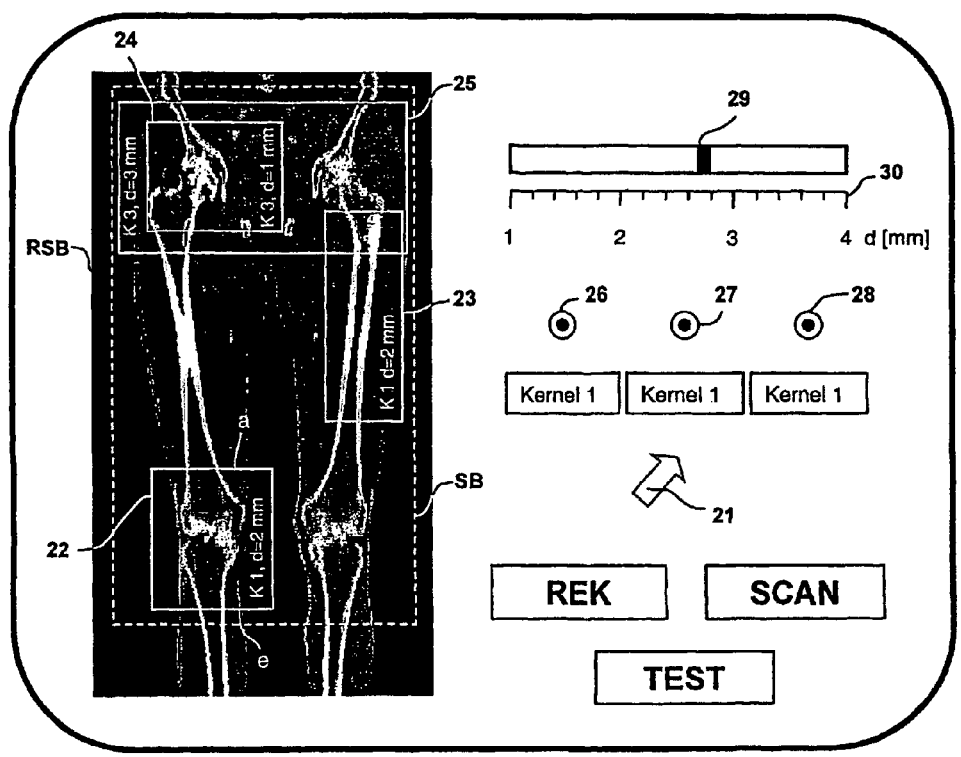

By using the X-ray shadow image RSB obtained in the manner described previously, it is possible, in the way illustrated in FIG. 4 by means of the mouse 20, the associated cursor is again designated 21, for example to mark rectangular reconstruction regions, for example 22, 23, 24 and 25, in the X-ray shadow image RSB within the region SB with respect to which volume data has been recorded in the course of the spiral scan, with respect to which regions the reconstruction of image data is to take place on the basis of the volume data recorded.

The individual reconstruction regions 22 to 25 can be allocated individual reconstruction parameters by an operator by actuating corresponding operating elements displayed on the monitor.

As an example, FIG. 4 illustrates, as reconstruction parameters, the convolution core to be used in the reconstruction of the respective reconstruction region, kernel 1, kernel 2, kernel 3, and the reconstructed layer thickness d on which the reconstruction of the respective reconstruction region is based. The reconstructed layer thickness d is the half-value width of the layer sensitivity profile and therefore that layer thickness from which the data in a reconstructed slice contain substantially originates.

Figure 5:
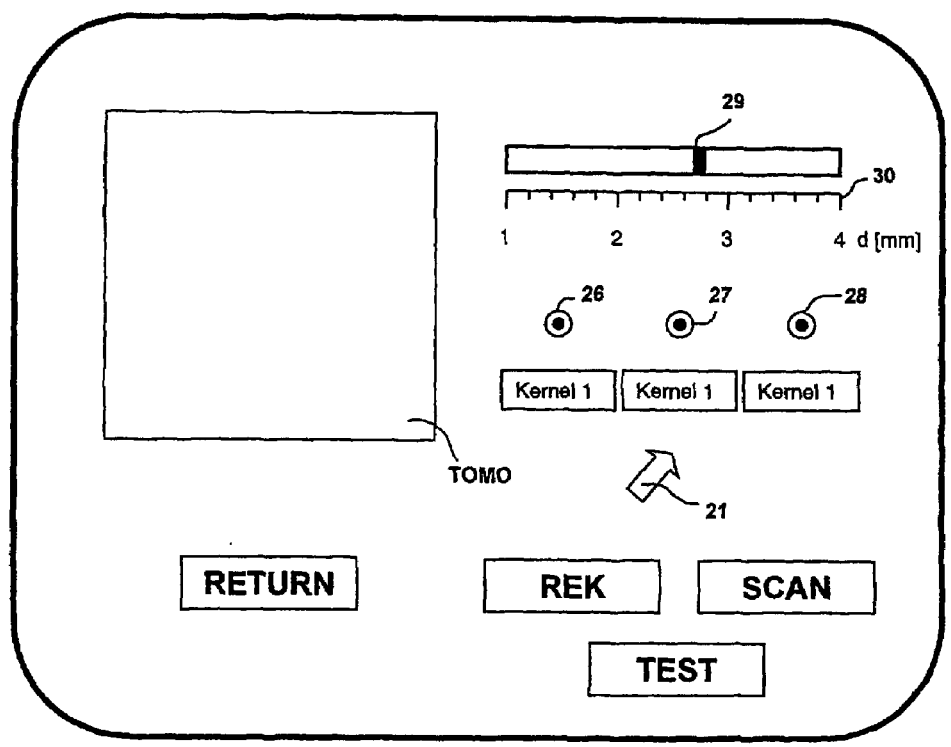

However, before the reconstruction of image data is carried out with respect to the marked reconstruction regions 22 to 25, there is the possibility of checking the correct position of the reconstruction regions 22 to 25, by a slice indicated only by its outlines in FIG. 5 and transmitted by TOMO, being reconstructed for the start and/or end of a reconstruction region 22 to 25, as viewed in the z direction, and displayed in the manner illustrated in FIG. 5 instead of the X-ray shadow image RSB. Such a slice, designated a test slice below, therefore represents a layer of the test object which, for example in the case of the start of the reconstruction region 22, contains its front end designated by a in FIG. 4 and, in the case of the end of the reconstruction region 22, contains its end designated by e in FIG. 4.

A return to the X-ray shadow image RSB and therefore the monitor display according to FIG. 4 is carried out by activating an icon designated RETURN by means of cursor 21 and mouse 20.

The production of test slices is carried out by, firstly, by means of cursor 21 and mouse 20, the icon TEST displayed on the monitor being activated and then the cursor 21 being moved to the start or the end of the respective reconstruction region of interest, the associated test slice being reconstructed and displayed in accordance with FIG. 5 in response to a mouse click.

In this way, with the aid of test slices, as required all or individual specially relevant reconstruction regions can be checked with regard to their correct start and/or end.

Should it be determined, on the basis of a test slice, that the start or the end of the associated reconstruction region was not chosen correctly, then there is the possibility of correcting the position and/or size of the marking corresponding to the respective reconstruction region and possibly checking again by using test slices which are to be produced anew and correspond to the changed conditions.

Once all the reconstruction regions have been chosen correctly, by means of cursor 21 and mouse 20 an icon designated REC and displayed on the monitor is activated, whereupon the image computer 11 uses the volume data recorded previously in the course of the spiral scan to reconstruct image data with respect to the reconstruction regions 22 to 25 in accordance with algorithms known to those skilled in the art, using as a basis the reconstruction parameters associated with the respective reconstruction region.

Reconstruction parameters are assigned to a reconstruction region 22 to 25 by the cursor 21 being moved onto the respective reconstruction region, for example the reconstruction region 23, and this reconstruction region being set into an activated state by actuating the right key of the mouse 20, whereupon, if a convolution core and a reconstructed layer thickness d have been chosen, these reconstruction parameters are assigned to the respective reconstruction region.

The reconstruction parameters are assigned to the respectively activated reconstruction region, as far as the convolution core is concerned, by the cursor 21 being moved onto the button 26 to 28 associated with the respectively desired convolution core kernel 1 to kernel 3 and said button being activated by clicking the left-hand key of the mouse 20.

As far as the reconstructed layer thickness is concerned, this is set by displacing a slider 29 on a scale 30 to the desired value, it being possible for the slider 29 to be adjusted by the cursor 21 being moved onto the slider 29 and the latter being displaced by actuating the left-hand key on the mouse 20.

As can be seen from FIG. 4, the reconstruction parameters assigned to the reconstruction regions 22 to 25 are displayed in the X-ray shadow image RSB within the reconstruction regions 22 to 25.

As can further be seen from FIG. 4, reconstruction regions can be defined which are completely separated from one another, such as the reconstruction regions 22 and 24. However, reconstruction regions can also overlap to some extent, as is the case in the reconstruction regions 23 and 25. In addition, reconstruction regions can be defined which overlap completely, that is to say are nested in one another, as is the case in the reconstruction regions 24 and 25.

In the case of the previously described operating mode of the device, the marking of the reconstruction regions is carried out on the basis of an X-ray shadow image obtained before the recording of the volume data.

For the case in which volume data with respect to a diagnostically relevant region is already present and, for example, is stored in the memory 14, the procedure in a second operating mode can also be such that an X-ray shadow image permitting the marking of reconstruction regions is derived from the volume data in accordance with a method known per se. The X-ray shadow image determined from the volume data is then displayed, in order to be able to mark the desired reconstruction regions therein, to check the correct position of the reconstruction regions by using reconstructed slices with respect to the start and the end of the respective region, and to assign reconstruction parameters to the marked reconstruction regions, whereupon the appropriate image data is reconstructed on the basis of the volume data already available. With this procedure, in the course of a diagnosis made on the basis of a volume data set that is present with respect to different reconstruction regions with associated reconstruction parameters or already previously reconstructed reconstruction regions with changed reconstruction parameters, it is possible to reconstruct image data without renewed recording of volume data being required, with the associated radiation exposure of the test object.

It therefore becomes clear that the method according to the invention makes it possible to define various reconstruction regions with the respectively suitable reconstruction parameters, and check them with regard to their correct position, in a graphical manner in a simple, flexible and comprehensible manner in volume data which is or has been recorded by means of a spiral scan, for example. In the process, it is not necessary for a plurality of reconstruction regions to be marked as described previously. Instead, it is also possible to mark only a single reconstruction region.

The construction of the image computer 11 in the case of the above exemplary embodiment was described as though the preprocessing unit 12 and the reconstruction unit 13 were hardware components. This can be so in fact. As a rule, however, the aforementioned components are implemented by software modules which run on a universal computer which is provided with the necessary interfaces and which, differing from FIG. 1, can also perform the function of the control unit 18, which is then superfluous.

The CT device in the case of the exemplary embodiment described has a detector system 5 with rows whose width measured in the z direction is of equal size and, for example, is 1 mm. Differing from this, within the scope of the invention a detector system can also be provided whose rows are of different width. For example, two inner rows each of 1 mm width and, on both sides of the latter, in each case a row of 2 mm width can be provided.

In the case of the exemplary embodiments described, the relative movement between the measuring unit 1 and the mounting device 9 is in each case produced by the mounting device 9 being displaced. However, within the scope of the invention, there is also the possibility of leaving the mounting device 9 in a fixed location and displacing the measuring unit 1 instead. In addition, within the scope of the invention there is the possibility of producing the necessary relative movement by displacing both the measuring unit 1 and the mounting device 9.

The exemplary embodiments described above are CT devices of the third generation, that is to say the X-ray source and the detector system are displaced jointly about the system axis during the production of images. However, the invention can also be used in connection with CT devices of the fourth generation, in which only the X-ray source is displaced about the system axis and interacts with a stationary detector ring, if the detector system is a two-dimensional array of detector elements.

The method according to the invention can also be used in CT devices of the fifth generation, that is to say CT devices in which the X radiation originates not only from one focus but from a plurality of foci of one or more X-ray sources displaced about the system axis, if the detector system has a two-dimensional array of detector elements.

The CT devices used in connection with the exemplary embodiments described above have a detector system with detector elements arranged in the manner of an orthogonal matrix. However, the invention can also be used in conjunction with CT devices whose detector system has detector elements arranged in a manner other than a two-dimensional array.

The exemplary embodiments described above relate to the medical application of the method according to the invention. However, the invention can also be applied outside medicine, for example in checking luggage or in material examination.

Although modifications and changes may be suggested by those skilled in the art, it is the invention of the inventor to embody within the patent warranted heron all changes and modifications as reasonably and properly come within the scope of his contribution to the art.

The invention claimed is:

1. A method of operating a CT device, by which volume data pertaining to a volume region of a test object are recorded, comprising the steps of:
   a) recording volume data pertaining to a volume region of a test object and creating and displaying a topogram of the volume region from the volume data,
   b) inserting at least one marking into the topogram X-ray shadow image for identifying a designated reconstruction region, with respect to which image data are to be reconstructed from volume data,
   c) reconstructing and displaying a slice of at least one of a start and an end of the designated reconstruction region from the volume data recorded, and
   d) reconstructing only image data pertaining to each designated reconstruction region.

2. The method as claimed in claim 1, comprising assigning at least one reconstruction parameter to said reconstruction region, and reconstructing only image data pertaining to the reconstruction region dependent on the reconstruction parameters assigned thereto.

3. The method as claimed in claim 2, comprising predefining at least one of a layer thickness and a convolution kernel as said at least one reconstruction parameter.

4. The method as claimed in claim 1 comprising marking a plurality of designated reconstruction regions.

5. The method as claimed in claim 4, comprising marking a plurality of designated reconstruction regions which at least partially overlap one another.

6. The method as claimed in claim 1 comprising recording the volume data in a spiral scan.

* * * * *